US00PP14977P2

(12) United States Plant Patent
Zerr

(10) Patent No.: US PP14,977 P2
(45) Date of Patent: Jul. 6, 2004

(54) POINSETTIA PLANT NAMED 'FISMARS'

(50) Latin Name: *Euphorbia pulcherrima*
Varietal Denomination: Fismars

(75) Inventor: Katharina Zerr, Höhr-Grenzhausen (DE)

(73) Assignee: Florfis AG (CH)

( * ) Notice: Subject to any disclaimer, the term of this patent is extended or adjusted under 35 U.S.C. 154(b) by 51 days.

(21) Appl. No.: 10/382,658

(22) Filed: Mar. 7, 2003

(51) Int. Cl.[7] ..... A01H 5/00
(52) U.S. Cl. ..... Plt./307
(58) Field of Search ..... Plt./307

*Primary Examiner*—Bruce R. Campell
*Assistant Examiner*—June Hwu
(74) *Attorney, Agent, or Firm*—Foley & Lardner

(57) ABSTRACT

A new and distinct Poinsettia plant named 'Fismars', characterized as having medium red bract color; medium sized bracts in tight and flat rosette-like arrangement; dark green foliage with weak lobes; about medium sized, V-shaped with the branches slanting upright; and begin of flowering mid season.

1 Drawing Sheet

Latin name of the genus and species of the plant claimed: *Euphorbia pulcherrima.*

Variety denomination: Fismars.

The present invention relates to a new and distinct cultivar of poinsettia plant known by the cultivar name 'Fismars', and botanically known as *Euphorbia pulcherrima.*

'Fismars' is a product of a planned breeding program which had the objective of creating new poinsettia cultivars with red flower color in combination with dark-green foliage and good cultivation ability. 'Fismars' originated from a hybridization made by the inventor, Katharina Zerr, in Hillscheid, Germany, in 1996.

The female parent is the poinsettia variety '490' (U.S. Plant Pat. No. 7,825), which is characterized by red bract color, dark-green foliage, and early flowering. The male parent is a proprietary poinsettia cultivar, designated No. '298' (unpatented), having bright red bracts, dark-green foliage, bracts and leaves with strong lobes, and upright plant habit with strong branch s.

The seeds germinated in the spring of 1997, and the resulting seedlings were selected during flowering period in the late summer of 1997. 'Fismars' was discovered and selected as a flowering plant within the progeny of the stated cross by Katharina Zerr. A cutting was taken from the seedling plant and grown out for examination of single-stem plants in the late fall to winter of 1997/98.

In the spring of 1999, more cuttings were taken from the chosen seedling and grafted on rootstocks of 'Beckmann's Altrosa', U.S. Plant Pat. No. 9,336, in order to enhance branching ability. From the upper area of the successfully grafted plants, shoot tip cuttings were taken for the cultivation of branched plants for the second examination in the fall of 1999.

Horticultural examination (of the clone) starting in 1999 and continuing thereafter has confirmed that the combination of characteristics as herein disclosed for 'Fismars' are firmly fixed and retained through successive generations of asexual reproduction.

BRIEF SUMMARY OF THE INVENTION

The following traits have been repeatedly observed and are determined to be basic characteristics of 'Fismars' which in combination distinguish this Poinsettia as a new and distinct cultivar:

1. Medium red bract color;
2. Medium siz d bracts in tight and flat rosette-like arrangem nt;
3. Dark green foliag with w ak lobes;
4. About medium sized, v-shaped with the branches slanting upright; and
5. Begin of flowering mid season 'Fismars' has not been observed under all possible environmental conditions. The phenotype may vary significantly with variations in environment such as temperature, light intensity, and day-length. The following observations, measurements and comparisons describe plants grown in Hillscheid, Germany, under greenhouse conditions which approximate those generally used in commercial practice.

Of the many commercial cultivars known to the inventor, the most similar in comparison to 'Fismars' is the parent cultivar '490' and the variety 'Fiscor' (U.S. Plant Pat. No. 9,364).

In comparison to parent cultivar '490' also known as 'Freedom Red', 'Fismars' has smaller bracts with very little rugosity, leaves with only weak expression of lobes, more uniform plant habit with more upright directed branches, and medium, instead of early, beginning of flowering.

In comparison to 'Fiscor', 'Fismars' has a slightly less intense bract color, less distinct lobing of bracts and leaves, and similar plant size, but different habit: it is less wide, more V-shaped, which means an advantage for packing and shipment.

BRIEF DESCRIPTION OF THE DRAWING

The accompanying color photographic drawing shows typical inflorescence and foliage of 'Fismars', with colors being as true as possible with illustrations of this type. The photograph shows a mature potted plant.

DETAILED BOTANICAL DESCRIPTION

The plants described had been grown in a greenhouse in Dorsten, Germany, from summer to fall of 2002. Rooted cuttings were planted into 13 cm pots on July 17, and were pinched on August 1, leaving 7–8 leaves. Initially, the temperature was between a minimum of 20° C. and 26° C. maximum (ventilation temperature), and lower from late September, minimum 18° C. to 24° C. maximum. Growth regulator was applied twice, in early and in late August. The plants initiated flowers under short-day conditions under natural short-day conditions in fall, no black cloth was applied.

Observations and measurements were mainly taken in early December, when the plants were in full flower and about 20 weeks old. In the following description color references are made to The Royal Horticultural Society Colour Chart (R.H.S.). The color values were determined indoors in a north light.

Plant:

*Form.*—Shrub, self-branching.

*Growth habit.*—About medium vigor, moderately compact structure, pinched plants are bushy with the branches upright directed at an angle of roughly 45°, foliage canopy uniformly rounded.

*Height in 13 cm pot, above soil line.*—26.4 cm.

*Width.*—44.8 cm.

*Average number of branches.*—8.0 on average.

*Length of branches.*—About 19–24 cm.

*Diameter of branches.*—6–8 mm.

*Average number of inflorescence.*—7.75 on average.

*Stem color.*—Lower part: green, RHS 143 B–143 C, upper part reddish infused, RHS 184 A.

*Rooting.*—Medium, sufficiently rooted for transplanting after about 20–24 days in a greenhouse at a temperature of 22–24° C.

*Blooming habit.*—Begin under natural short day conditions in fall: botanically (cyathia open) in early December commercially (bracts colored, marketable).

*Flowering response time.*—About 9–10 weeks.

*Flowering season.*—Mainly from late November to late December.

*Keeping quality.*—Good quality will be maintained for about 4–5 weeks.

Foliage:

*Shape.*—Ovate, with rounded to almost truncate base, very weak lobes and acuminate tip.

*Margin.*—Entire, apart from the lobes. Texture: Upper surface: smooth and flat, only weakly veined, lower surface flat and smooth, except for the slightly protruding midrib and finer side veins in a pinnate pattern.

*Vein coloration.*—Upper leaf surface veins are brownish-pink at the base: RHS 181A, lower leaf surface midrib is dull pink, RHS 181 C.

*Leaf blade length.*—11.0 cm on average.

*Leaf blade width.*—9.25 cm.

*Petiole.*—Length 4.5 cm on average.

*Quantity.*—About 50 leaves per plant.

*Color.*—Generally dark green, uniform. Mature foliage: Upper surface, near RHS 139 A, under surface, RHS 139 B. New foliage: Upper surface: RHS 143 A, under surface: RHS 137 D.

*Leaf petiole.*—Upper side purple, RHS 53 A lower side: purple-pink, RHS 53 C.

*Aspect.*—Petioles are horizontally directed, while the leaf blades showing slightly downwards.

Disease resistance: No special observations made.

Flowering description:

*Whole inflorescence with surrounding bracts.*—About medium-sized, star-shaped, flat, with the bracts horizontally directed in a tight arrangement, and overlapping.

*Diameter.*—Approximatelv 21–23 cm.

*Height of inflorescence.*—20–30 mm (relatively flat).

*Number of bracts per inflorescence.*—10–12 (size over 2 cm).

*Keeping quality.*—Keeps well throughout December or longer.

Bracts:

*Shape.*—Ovate, with rounded bases, very weak to weak lobes, and acuminate tips.

*Size.*—10.5–11.0 cm long, 7.5–8.0 cm wide.

*Texture.*—Flat and smooth, very little rugosity with maturing of the bract, Upper surface: vein color corresponds closely to the bract color, Lower surface: vein color pink, about RHS 185 C.

*Color.*—Generally medium-red, uniform, occasionally slightly lighter near margin. Upp r surface: Between RHS 46 B and RHS 46 C. Lower surface: RHS 46 D.

*Petiole.*—12–15 mm long; color: upper side dark red, RHS 46 A, lower side dull pink, near RHS 51 B.

Cyme: 15–22 mm in diameter, 5–8 cyathia borne in a tight cluster.

*Cyathium.*—Ovate, about 6–7 mm in diameter, medium to light green colored, RHS 143 B, top red, RHS 46 B.

*Peduncle.*—Light green, RHS 143 C, only 1–2 mm long.

*Nectar cups.*—One or two per cyathium up to 6 mm wide, bright yellow, RHS 12 A, no reddish coloring at the margin.

Reproductive organs:

*Stamens.*—About 10–20 in a cluster, red filaments, RHS 46 B, moderate pollen, yellow RHS 12 A.

*Female flowers.*—No observations made to date.

*Fruit/seed set.*—No seed set observed.

I claim:

1. A new and distinct Poinsettia plant named 'Fismars' as illustrated and described herein.

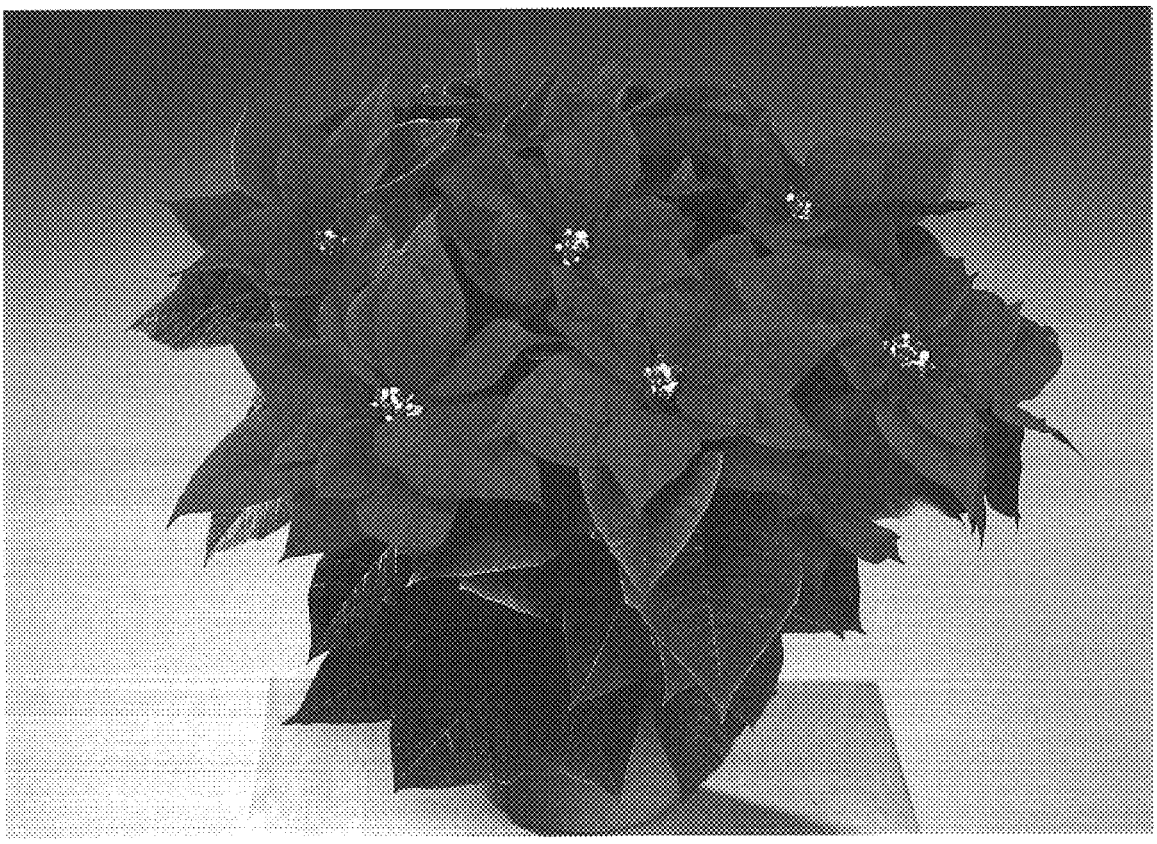

* * * * *